(12) United States Patent
Qian

(10) Patent No.: US 10,849,833 B2
(45) Date of Patent: Dec. 1, 2020

(54) MANUFACTURING METHOD OF PRESERVATIVE-FREE FACIAL MASK AND PROCESS EQUIPMENT THEREOF

(71) Applicant: Fengying Qian, Guangzhou (CN)

(72) Inventor: Fengying Qian, Guangzhou (CN)

(*) Notice: Subject to any disclaimer, the term of this patent is extended or adjusted under 35 U.S.C. 154(b) by 469 days.

(21) Appl. No.: 15/846,183

(22) Filed: Dec. 18, 2017

(65) Prior Publication Data
US 2019/0183745 A1 Jun. 20, 2019

(51) Int. Cl.
A61K 8/02 (2006.01)
A41H 42/00 (2006.01)
A61Q 19/00 (2006.01)
A61K 8/73 (2006.01)
A61K 8/92 (2006.01)
A61K 8/60 (2006.01)
A61K 8/67 (2006.01)
A61K 8/65 (2006.01)
A61K 8/9706 (2017.01)
A61K 8/40 (2006.01)
A61K 8/34 (2006.01)
A41D 13/11 (2006.01)

(52) U.S. Cl.
CPC ............ A61K 8/0212 (2013.01); A41D 13/11 (2013.01); A41H 42/00 (2013.01); A61K 8/345 (2013.01); A61K 8/40 (2013.01); A61K 8/60 (2013.01); A61K 8/65 (2013.01); A61K 8/67 (2013.01); A61K 8/73 (2013.01); A61K 8/731 (2013.01); A61K 8/732 (2013.01); A61K 8/735 (2013.01); A61K 8/925 (2013.01); A61K 8/9706 (2017.08); A61Q 19/00 (2013.01); A41D 2500/30 (2013.01); A61K 2800/30 (2013.01)

(58) Field of Classification Search
None
See application file for complete search history.

(56) References Cited

FOREIGN PATENT DOCUMENTS

CN 104546560 A * 4/2015
CN 204840340 U * 12/2015

OTHER PUBLICATIONS

Machine Translation of CN 104546560 A (Year: 2015).*
Machine Translation of CN 204840340 U (Year: 2015).*

* cited by examiner

Primary Examiner — Shamim Ahmed
Assistant Examiner — Bradford M Gates
(74) Attorney, Agent, or Firm — Wayne & Ken, LLC; Tony Hom

(57) ABSTRACT

The invention discloses a manufacturing method of a preservative-free facial mask and process equipment thereof. The method includes preparing distilled water with boiling point of 80-100° C., and reserving at a constant temperature; transporting the distilled water into a mixing agitator, cooling to 45-55° C.; weighing a facial mask powder into a drying mixer and mixing; turning on the mixing agitator, stirring the distilled water, adding the facial mask powder and a facial mask liquid material, stirring to form a paste liquid; importing the paste liquid into a colloid grinder, and forming a facial mask slurry; transporting into a coating machine, spreading the facial mask slurry onto surface of non-woven cloth to form facial mask slurry layer; drying the non-woven cloth, and performing instantaneous high-temperature sterilization and rolling up; slicing, moulding and packaging. The invention protects the human skin from being harmed and has a better effect without containing preservatives.

5 Claims, 1 Drawing Sheet

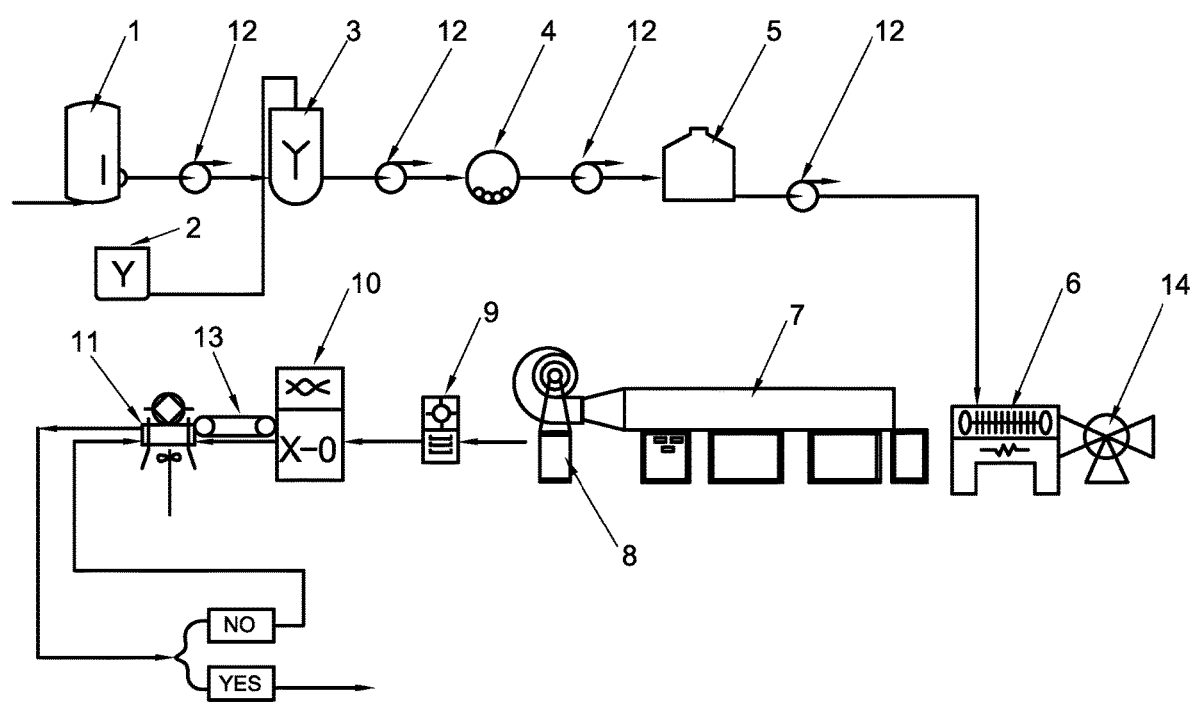

MANUFACTURING METHOD OF PRESERVATIVE-FREE FACIAL MASK AND PROCESS EQUIPMENT THEREOF

FIELD OF THE INVENTION

The present invention relates to a manufacturing method of a preservative-free facial mask and process equipment thereof.

BACKGROUND OF THE INVENTION

The liquid and paste of the traditional facial masks contain a lot of water, the product must be added with preservative ingredients, such as nipagin (methyl ester, ethyl ester, lactone etc.), to ensure the liquid and paste to be fresh. As everyone knows, preservatives are harmful to the human body and frequent use can damage skin tissue, in Darbre's study in 2004, five common components of parabens detected in breast cancer tissue led to a debate in the international cosmetic industry about the safety of paraben esters.

Scientific Committee on Consumer Safety (SCCS) evaluated the safety of the paraben esters in 2010, 2011 and 2013 respectively, product dosage is constantly adjusted. In May 2013, recommendations for the use of nepodilate substances in SCCS/1514/13 is that: methylparaben and ethylparaben are safe at the maximum regulatory dosage, with methylparaben: 0.4%, ethylparaben: 0.4%; propyl parabens and butyl parabens are safe when doses are less than 0.19% (calculated based on ester) when used alone or in combination; research data on para-hydroxyisopropyl, para-hydroxy-isobutyl and phenyl-parahydroxybenzoates are not enough and safety is unknown. EU adopts suggestions for methylparaben and ethylparaben in SCCS/1514/13 in its 1223/2009 Regulation, meanwhile, it is also proposed that the maximum dose of the propyl paraben and butyl paraben is less than 0.14% (calculated based on acid) when used alone or in combination, and propyl paraben and butyl paraben are forbidden to be used in retention-type diapers for children under 3 years of age. Cosmetic Ingredient Review (CIR) didn't evaluate the safety of parabens within the past 5 years, The latest safety assessment was updated in 2008, the conclusion is that it is safe to use at the maximum (0.4% alone and 0.8% total). As the EU expert group believes that paraben esters have been shown to have some reproductive effects on experimental rats as a result of recent studies, the long-term use of preservatives has adverse effects on the human body.

And the traditional facial mask is immersed in the non-woven fabric, the facial mask is thicker and adhesion is uneven, the facial mask can not be fully used, resulting in a lot of waste and increasing production costs and consumption costs.

SUMMARY OF THE INVENTION

The purpose of the present disclosure is to solve the following problems: the existing facial masks contain a variety of preservatives which hurt human skin; the existing facial masks are thicker and uneven, resulting in waste of raw materials and increasing consumer costs, therefore, the present disclosure provides a preservative-free facial mask and process equipment thereof.

A manufacturing method of a preservative-free facial mask comprises the following steps:

step a. preparing distilled water with boiling point of 80-100° C., and reserving at a constant temperature;

step b. quantitatively transporting the distilled water of 80-100° C. into a mixing agitator according to a list of ingredients, cooling to 45-55° C.;

step c. accurately weighing a facial mask powder, adding the weighed facial mask powder into a drying mixer according to the list of ingredients, and mixing evenly for use;

step d. turning on the mixing agitator, stirring the distilled water slowly, adding the facial mask powder mixed evenly by the drying mixer into the distilled water in the mixing agitator, stirring and mixing evenly, adding a facial mask liquid material, and mixing and stirring rapidly to form a paste liquid;

step e. importing the paste liquid into a colloid grinder to perform grinding, transferring the grinded paste liquid into a static liquid storage tank to defoam and forming a facial mask slurry;

step f. transporting the facial mask slurry into a coating machine, evenly spreading the facial mask slurry onto a surface of a non-woven cloth to form a facial mask slurry layer;

step g. transporting the non-woven cloth coated with the facial mask slurry into a fully closed thermostatic steam dryer, drying at 80-100° C. to form a facial mask, performing instantaneous high-temperature sterilization and rolling up the facial mask by a film rolling machine to form a facial mask roll; and step h. slicing and moulding the dried facial mask roll when a moisture content of the dried facial mask roll is less than 3%, and packaging.

Further, the facial mask powder comprises plant dietary cellulose, water-soluble lanolin, Carboxyl Methyl Cellulose (CMC), plant modified starch, glucose, vitamin, collagen, seaweed, agar, pullulan and xanthan gum.

Further, the facial mask liquid material comprises essential oil, ammonia ketone, propylene glycol, sodium hyaluronate and glycerinum.

Further, in the step f, the facial mask slurry is fully absorbed in the non-woven cloth by a high-permeation process, and the thickness of the facial mask slurry layer is 0.5-1.5 mm.

Further, in the step f, the non-woven cloth coated with is transported to the fully enclosed thermostatic steam dryer for 10-15 minutes.

A process equipment of the manufacturing method of the preservative-free facial mask comprises a steam-jacketed kettle, a drying mixer, a mixing agitator, a colloid grinder, a static liquid storage tank, a facial mask coating machine, a drying machine and a film rolling machine; output ends of the steam-jacketed kettle and the drying mixer are connected into the same mixing agitator, an output end of the mixing agitator is successively connected with the colloid grinder, the static liquid storage tank, the facial mask coating machine, the drying machine and the film rolling machine; an output end of the film rolling machine is successively provided with a moisture tester, a facial mask slicing machine and a packaging machine, and an assembly line for the facial mask is formed.

Further, the drying machine is a closed tunnel-type thermostatic steam drying machine.

Further, the steam-jacketed kettle, the drying mixer, the mixing agitator, the colloid grinder and the static liquid storage tank transport material by delivery pipes, outlets of the delivery pipes are provided with controlling feeding pumps or/and control valves.

Further, an output end of the facial mask slicing machine transfers material to the packaging machine through a conveyer belt, forming automatic delivery and packaging.

Further, the facial mask coating machine comprises a non-woven cloth rolling delivery machine for automatically transporting the non-woven cloth.

The present disclosure has the following salient substantive features and significant improvements:

1. The facial mask powder of the present disclosure comprises plant dietary cellulose, water-soluble lanolin, CMC, plant modified starch, glucose, vitamin, collagen, seaweed, agar, pullulan, xanthan gum; and the facial mask liquid material comprises essential oil, ammonia ketone, propylene glycol, sodium hyaluronate and glycerinum. Human skin is better protected and using effect is better without preservatives.

2. The present disclosure includes a steam-jacketed kettle, a drying mixer, a mixing agitator, a colloid grinder, a static liquid storage tank, a facial mask coating machine, a drying machine and a film rolling machine; output ends of the steam-jacketed kettle and the drying mixer are connected into the same mixing agitator. An output end of the mixing agitator (3) is successively connected with the colloid grinder, the static liquid storage tank, the facial mask coating machine, the drying machine and the film rolling machine. An output end of the film rolling machine is successively provided with a moisture tester, a facial mask slicing machine and a packaging machine, thus forming a facial mask pipeline processing and automatic production. Production efficiency is high, coating facial mask layer is more uniform, the waste facial mask material can be better avoided, cost is saved, thereby reducing the cost of consumer.

3. The present disclosure adopts advanced fully enclosed tunnel-type thermostatic drying facial mask technology, instantaneous high temperature sterilization process is adopted in the production process, especially the moisture content of the facial mask product is lower than 3.0%, it does not provide the environment of growth and reproduction for any microbial bacteria. Therefore, the facial mask in the present disclosure needs no any preservative ingredients, which not only ensures the anti-corrosion and anti-bacterial effect of the facial mask, but also has no impact on the human body, and the facial mask is safely used.

BRIEF DESCRIPTION OF THE DRAWINGS

FIG. 1 is a schematic diagram of the process equipment of the present invention.

DETAILED DESCRIPTION OF THE INVENTION

The present invention is further described in detail with reference to the accompanying drawings.

As reference to FIG. 1, a process equipment of the manufacturing method of the preservative-free facial mask comprises a steam-jacketed kettle (1), a drying mixer (2), a mixing agitator (3), a colloid grinder (4), a static liquid storage tank (5), a facial mask coating machine (6), a drying machine (7) and a film rolling machine (8); output ends of the steam-jacketed kettle (1) and the drying mixer (2) are connected into the same mixing agitator (3), an output end of the mixing agitator (3) is successively connected with the colloid grinder (4), the static liquid storage tank (5), the facial mask coating machine (6), the drying machine (7) and the film rolling machine (8); an output end of the film rolling machine (8) is successively provided with a moisture tester (9), a facial mask slicing machine (10) and a packaging machine (11), and an assembly line for the facial mask is formed.

In embodiments, the drying machine (7) is a closed tunnel-type thermostatic steam drying machine.

In order to achieve the automated production equipment, the steam-jacketed kettle (1), the drying mixer (2), the mixing agitator (3), the colloid grinder (4) and the static liquid storage tank (5) transport material by delivery pipes, outlets of the delivery pipes are provided with controlling feeding pumps (12) or/and control valves. An output end of the facial mask slicing machine (10) transfers material to the packaging machine (11) through a conveyer belt (13), forming automatic delivery and packaging. The facial mask coating machine (6) comprises a non-woven cloth rolling delivery machine (14) for automatically transporting the non-woven cloth.

A manufacturing method of a preservative-free facial mask comprises the following steps:

step a. preparing distilled water with boiling point of 80-100° C., and reserving at a constant temperature;

step b. quantitatively transporting the distilled water of 80-100° C. into a mixing agitator according to a list of ingredients, cooling to 45-55° C.;

step c. accurately weighing a facial mask powder, adding the weighed facial mask powder into a drying mixer according to the list of ingredients, and mixing evenly for use;

step d. turning on the mixing agitator, stirring the distilled water slowly, adding the facial mask powder mixed evenly by the drying mixer into the distilled water in the mixing agitator, stirring and mixing evenly, adding a facial mask liquid material, and mixing and stirring rapidly to form a paste liquid;

step e. importing the paste liquid into a colloid grinder to perform grinding, transferring the grinded paste liquid into a static liquid storage tank to defoam and forming a facial mask slurry;

step f. transporting the facial mask slurry into a coating machine, evenly spreading the facial mask slurry onto a surface of a non-woven cloth to form a facial mask slurry layer;

step g. transporting the non-woven cloth coated with the facial mask slurry into a fully closed thermostatic steam dryer, drying at 80-100° C. to form a facial mask, performing instantaneous high-temperature sterilization and rolling up the facial mask by a film rolling machine to form a facial mask roll; and step h. slicing and moulding the dried facial mask roll when a moisture content of the dried facial mask roll is less than 3%, and packaging.

In the method, the facial mask powder comprises plant dietary cellulose, water-soluble lanolin, Carboxyl Methyl Cellulose (CMC), plant modified starch, glucose, vitamin, collagen, seaweed, agar, pullulan and xanthan gum. The facial mask liquid material comprises essential oil, ammonia ketone, propylene glycol, sodium hyaluronate and glycerinum.

In the step f, the facial mask slurry is fully absorbed in the non-woven cloth by a high-permeation process, and the thickness of the facial mask slurry layer is 0.5-1.5 mm; the non-woven cloth coated with is transported to the fully enclosed thermostatic steam dryer for 10-15 minutes.

The present invention is completely developed using all-natural plant raw materials and food-grade raw materials without any chemical hazards to the human body. In the production process, the essential oils, plant extracts, sodium hyaluronate, collagen protein, vitamins and trace elements and other beneficial elements of the human body and so on are completely absorbed in the non-woven using high permeability process. In the production process, the instantaneous high-temperature sterilization process is adopted, especially the drying process adopts fully enclosed tunnel-type thermostatic drying facial mask process, so that the final moisture content in the facial mask is lower than 3%, it does not provide growth and reproduction environment for any microbial. Therefore, the facial mask in the present disclosure needs no any preservative ingredients, which not only ensures the anti-corrosion and anti-bacterial effect of the facial mask, but also has no impact on the human body, and the facial mask is safely used.

The specific process of the present invention is:

1. Transporting the pure water into the steam-jacketed kettle (1) through a pipe, and heating to the boiling point of 100° C. through high temperature steam, and maintaining at a constant temperature for later use;

2. according to the list of ingredients, quantitatively pumping 100° C. hot water into the mixing agitator, and cooling to 50° C. for later use;

3. according to the list of ingredients, accurately weighing plant dietary cellulose, water-soluble lanolin, Carboxyl Methyl Cellulose (CMC), plant modified starch, glucose, vitamin, collagen, seaweed, agar, pullulan and xanthan gum, and adding into the drying mixer, turning on the power source, mixing for 5 min, stopping for later use;

4. turning on the power source of the mixing agitator, shifting to 1 gear for stirring slowly, slowly adding the facial mask powder mixed uniformly in the drying mixer into the mixing agitator, slowly stirring uniformly, further adding the weight essential oil, ammonia ketone, propylene glycol, sodium hyaluronate and glycerinum after the materials are added completely, shifting to 2 gear for stirring for 10 min (that is accelerated stirring) to form the paste liquid, so that the granular particles of the facial mask powder can not be seen in the facial mask liquid material;

5. pumping the paste liquid mixed uniformly into the colloid grinder through the pipeline feeding pump, pumping the facial mask slurry into the static liquid storage tank for still standing and defoaming after grinding, and standing for 30 min for later use;

6. transporting the static facial mask slurry into the facial mask coating machine, uniformly spreading the facial mask slurry on the surface of the non-woven cloth to form a facial mask slurry layer, the thickness of the facial mask slurry layer is about 1.0 mm, transporting the non-woven cloth coated with the facial mask slurry into fully closed thermostatic steam drying machine through the automatic convey belt, rolling up the facial mask by the film rolling machine after dry sterilizing at 100° C. for 10 min;

7. quickly measuring the moisture content of the dried facial mask roll by the moisture tester, performing slicing and moulding process when the moisture content of the dried facial mask roll is less than 3%; and 8. performing the inner packaging process of the sliced and molded facial mask, packaging and putting in the warehouse after finished product is tested to be qualified, returning to the inner packaging and reworking if the finished product is tested to be unqualified.

What is claimed is:

1. A manufacturing method of a preservative-free facial mask, comprising the following steps:
    step a. preparing distilled water with a boiling point of 80-100° C., and reserving at a constant temperature;
    step b. quantitatively transporting the distilled water with a boiling point of 80-100° C. into a mixing agitator according to a list of ingredients, and cooling to 45-55° C.;
    step c. accurately weighing a facial mask powder, adding the weighed facial mask powder into a drying mixer according to the list of ingredients, and mixing evenly for use;
    step d. turning on the mixing agitator, stirring the distilled water, adding the facial mask powder mixed evenly by the drying mixer into the distilled water in the mixing agitator, stirring and mixing evenly, adding a facial mask liquid material, and mixing and stirring to form a paste liquid;
    step e. importing the paste liquid into a colloid grinder to perform grinding, transferring the grinded paste liquid into a static liquid storage tank to defoam and forming a facial mask slurry;
    step f. transporting the facial mask slurry into a coating machine, and evenly spreading the facial mask slurry onto a surface of a non-woven cloth to form a facial mask slurry layer;
    step g. transporting the non-woven cloth coated with the facial mask slurry into a fully closed thermostatic steam dryer, drying at 80-100° C. to form a facial mask, performing instantaneous sterilization and rolling up the facial mask by a film rolling machine to form a facial mask roll; and
    step h. slicing and moulding the dried facial mask roll when a moisture content of the dried facial mask roll is less than 3%, and packaging.

2. The manufacturing method of the preservative-free facial mask according to claim 1, wherein, the facial mask powder comprises plant dietary cellulose, water-soluble lanolin, Carboxyl Methyl Cellulose (CMC), plant modified starch, glucose, vitamin, collagen, seaweed, agar, pullulan and xanthan gum.

3. The manufacturing method of the preservative-free facial mask according to claim 1, wherein, the facial mask liquid material comprises essential oil, ammonia ketone, propylene glycol, sodium hyaluronate and glycerinum.

4. The manufacturing method of the preservative-free facial mask according to claim 1, wherein, in the step f, the facial mask slurry is fully absorbed in the non-woven cloth by a permeation process, and the thickness of the facial mask slurry layer is 0.5-1.5 mm.

5. The manufacturing method of the preservative-free facial mask according to claim 1, wherein, in the step g, the non-woven cloth coated with the facial mask slurry is transported to the fully closed thermostatic steam dryer for 10-15 minutes.

* * * * *